United States Patent [19]

Briska et al.

[11] 4,169,228
[45] Sep. 25, 1979

[54] X-RAY ANALYZER FOR TESTING LAYERED STRUCTURES

[75] Inventors: Marian Briska, Boeblingen; Armin Bohg, Neuweiler, both of Fed. Rep. of Germany

[73] Assignee: International Business Machines Corporation, Armonk, N.Y.

[21] Appl. No.: 912,899

[22] Filed: Jun. 5, 1978

[51] Int. Cl.² .............................................. G01N 23/20
[52] U.S. Cl. ................................... 250/272; 250/273
[58] Field of Search .............. 250/272, 273, 274, 277, 250/277 CH, 278, 279, 280

[56] References Cited
U.S. PATENT DOCUMENTS

| | | | |
|---|---|---|---|
| 3,525,863 | 8/1970 | Constantine et al. | 250/272 |
| 3,663,812 | 5/1972 | Koenig et al. | 250/280 |
| 3,765,773 | 10/1973 | Weiner | 356/114 |
| 3,839,635 | 10/1974 | Chan et al. | 250/278 |
| 3,963,922 | 6/1976 | Zulliger et al. | 250/272 |
| 4,028,547 | 6/1977 | Eisenberger | 250/272 |

OTHER PUBLICATIONS

L. G. Parratt, "Surface Studies of Solids by Total Reflection of X-Rays," published in Physical Review, Jul. 15, 1954.

Primary Examiner—Craig E. Church
Assistant Examiner—Thomas P. O'Hare
Attorney, Agent, or Firm—Henry Powers

[57] ABSTRACT

X-ray fluorescence produced by a primary X-ray beam incident at a very flat angle (below 1°) onto the surface of a specimen contained in a vacuum chamber is used to analyze shallow layers and/or to determine depths of shallow surface layers, such as a very thin (typically between about 10Å and 10³Å) silicon coating on Al or Cu layers which overlay a silicon substrate. Semiconductor profile determination may be another application of the invention.

11 Claims, 7 Drawing Figures

X-RAY ANALYZER FOR TESTING LAYERED STRUCTURES

FIELD OF THE INVENTION

The invention relates to an apparatus for X-ray fluorescence analysis.

DESCRIPTION OF THE PRIOR ART

For examining shallow or thin layers, a great variety of processes are known. First, there exists an electron beam microprobe where an electron beam of typically 30 keV is used for exciting a characteristic x-ray radiation. There is, however, the disadvantage of the relatively high background radiation caused by Bremsstrahlung so that a respective sensitivity reduction is observed; and the forming of a contamination layer due to interaction of the electron beam with the residual gas in the vacuum chamber is furthermore unavoidable; and where the analyzing depth cannot be reduced to much less than 1 μm below the irradiated surface, the considerable electron scattering taking place, does not permit clear results.

The Auger electron spectroscopey represents a process which when applied to light elements only permits a sensitive display. Furthermore, only a semiquantitative statement on the top automatic layer with a thickness of approximately 5 Å is obtainable. Deeper layer ranges are not at all accessible to examination without destruction by means of this process. Secondary ion mass spectrometry, however, uses an ion beam of typically 15 keV which knocks particles out of the sample to be examined by subsequent application of mass spectrometry analysis. Quite obviously, this method is not destruction-free. In addition, the classification of individual particles with individual sectors of the spectrum is frequently ambiguous with respect to the sample composition, but at any rate quite complicated.

Another process of layer examination is the proton or helium backscatter method where a highly energetic beam of $H^+$ or $He^+$ ions is directed at the sample. The energy losses of backscattered ions will then permit conclusions on the composition of shallow layers down to a depth of approximately 1 μm. In layer material of compositions of more than 3 elements, simultaneous detection of such leads to quantitative results under quite specific conditions but it is inapplicable for element concentrations in a layer which are substantially smaller than 1%. The low penetration depth does not permit a disturbance-free investigation when layer thicknesses of more than 1 μm are to be examined.

Although high penetration depths for the primary x-ray radiation can be achieved when x-ray fluorescence analysis processes are used, the analysis of shallow diffusions in semiconductors or of thin films is not possible for precisely this reason as this process is not sufficiently sensitive for this purpose. There is also the additional fact that in a laminate structure, the background radiation of layers other than the respective layer to be examined appears as a disturbing factor which has to be taken in consideration.

According to the article "Meβtechnische und instrumentelle Probleme der Rontgenfluoreszenz-Analyse" by Gerhard Lang in "Zeitschrift fur Instrumentenkunde", Vol. 70 (1962), No. 12, the functional principle of a typical apparatus for x-ray fluorescence analysis is characterized as follows: The x-ray tube irradiates a planar surface of the sample and excites the atoms contained therein to emit an x-ray fluorescence radiation (also called characteristic radiation or intrinsic radiation) which emanates from the probe in all directions. Via a collimator, the fluorescence radiation is directed to an analyzer crystal which depending on the angle—Bragg reflection condition—at which the radiation impinging on its lattice planes, reflects a radiation of a different wave length onto a beam detector. In order to be able to cover a larger range of the spectrum, the analyzer crystal is turned by means of a goniometer simultaneously with the detector in such a manner that the reflected radiation can reach the beam detector under any angle of incidence. This basic principle can be applied in many ways.

U.S. Pat. No. 3,525,863, to give an example, describes an x-ray fluorescence analysis apparatus by means of which the concentration of a respective element in a sample can be determined. For this purpose, a differential measuring process is employed where two monochromatic x-rays, one having a wavelength slightly above the absorption edge of the respective element and the other a wavelength slightly below the absorption edge of the respective element, are each made to act as parallelized beams on the sample in different periods. Both the backscattered x-ray fluorescence radiation generated in this process and the characteristic x-ray fluorescence generated are then collected by a common beam detector whose output signal, modulated by the difference in the incidence radiation, indicates the concentration of the respective element in the sample. Owing to this dual x-ray method the process, however, is rather complex without permitting the execution or extension of analyses in shallow areas of a sample for all elements contained therein.

U.S. Pat. No. 3,963,922 also describes an apparatus for x-ray fluorescence analysis, where x-ray source and sample are housed in the same vacuum vessel for permitting the detection, also of light elements in the sample, without having to accept an x-ray absorption between x-ray source and sample. Theoretically, the process described permits the detection of all element concentrations in the sample owing to the high penetration depth, but it also involves the problem that characteristic fluorescence radiation of an element can be superimposed by the characteristic x-ray fluorescence radiation of another element, e.g. in the case of impurities diffused into semiconductor samples, or in the case where shallow layers consisting of a specific material cannot be detected when they are separated from a substrate of the same material by layers of other materials. In both cases, an analysis is practically impossible.

SUMMARY OF THE INVENTION

It is the object of the invention to provide an x-ray fluorescence analysis arrangement with which a destruction-free analysis of a sample is possible down to a depth of substantial μm, and furthermore layers without the influence of disturbing background radiation can be examined so that the output signals in the entire measurement range always maintain a satisfactory signal-to-noise ratio.

In accordance with the invention, this object is achieved by means of an x-ray fluorescence analysis apparatus described and claimed herein.

Therefore, the arrangement is of such a nature that the characteristic x-ray fluorescence radiation excited by the incident primary x-ray beam is only used for analyzing the sample, whereas the additional excited scattering radiation is intercepted either by the wall of the chamber containing the arrangement, or by an absorption screen specifically provided for the purpose, e.g. a lead plate. According to the invention, the effective analyzing depth can be reduced down to a few Ås, in that the parallel primary radiation impinges on the sample at a discretionary flat angle near to, or below the angle of the total reflection. The angular degree and consequently the analyzing depth, however, depend on the material of the sample. For also detecting light elements in a sample, an evacuated or helium-filled chamber is provided in accordance with one preferred embodiment of the invention containing at least the sample fixed on a first height-adjustable goniometer, this goniometer itself being provided on a table shiftable in the direction of the goniometer plane and perpendicular to the sample plane, and the primary beams being incident in the goniometer plane. By means of such an arrangement, it is ensured that the entire sample surface of the strictly parallel, and due to a diaphragm arranged in series, sharply focused primary radiation can be emitted in successive scanning intervals. As the x-ray source, an x-ray tube or any other radiation source can be used, e.g. the target or the respective wall zone of an electron accelerator, or a synchroton radiation. The vacuum or helium chamber itself, however, requires a window for the incident primary radiation.

It is advantageous for many types of measurings (including semiconductor profile determinations) if any energy dispersive beam detector is fixed, in a manner known per se, to a cooling finger whose other end is maintained at the temperature of a liquefied gas, if necessary, by a Dewar vessel arranged outside the vacuum chamber.

In accordance with another embodiment of the invention, an x-ray tube serving as radiation source can be directed in a manner known per se to another goniometer inside or outside the chamber, that goniometer showing on its mounting table a crystal for the x-ray parallelization, utilizing the Bragg reflection condition; and in the beam path, from crystal to sample, a slidable x-ray diaphragm can be provided. In this manner, a fully integrated analysis measuring device is obtained which in many cases facilitates the analysis. Also arranging the second goniometer with its parallelization crystal and x-ray source in a vacuum or helium chamber, respectively, is of advantage when soft x-ray radiation is to be used for the analysis.

The parallelization crystal for the primary radiation, as used in the apparatus according to the invention, can be used either in the transmission, or in the reflection process, the latter being advantageous owing to its lower radiation losses.

Another way of parallelizing the primary beams consists in providing in the beam path between x-ray source and sample a collimator known per se, which would, for example, be advisable if a low intensity x-ray tube with polychromatic x-rays were to be provided as radiation source.

The arrangement as disclosed by the invention can be used in many ways. For the determination of the profiles of semiconductor components, to give an example, the individual diffusion zones can be determined in a destruction-free manner, with respect to their geometric and physical characteristics in a semiconductor wafer or in a semiconductor chip. Surface impurities of semiconductors or also of semiconductor components can advantageously be detected by means of the invention. A further advantageous use consists in the simultaneous determination and analysis of thin multilayer films, e.g. of thin silicon layers on metallization layers, which in turn are provided on silicon substrates. Due to the low penetration depth attainable by the incident primary beams, the substrate itself it not excited to emit its characteristic x-ray fluorescence radiation, the upper silicon layer can be perfectly analyzed.

In summary, the following advantages are made possible by the invention which could not be achieved by means of formerly existing apparatus: a destruction-free analysis of shallow areas down to a depth of a few $\mu$ms can be carried out with a satisfactory signal-to-noise ratio. The analyzing depth is selectable within a wide range. In the analysis, quantitative results are obtained. Unknown elements can be clearly identified from their characteristic K or L lines of the spectrum, a simple evaluation of the appearing spectra being possible as in the formerly used x-ray fluorescence analysis.

Below, the invention will be described in detail by means of an embodiment specification, on the basis of the drawings enumerated below.

DESCRIPTION OF PREFERRED EMBODIMENTS

Figure 1:
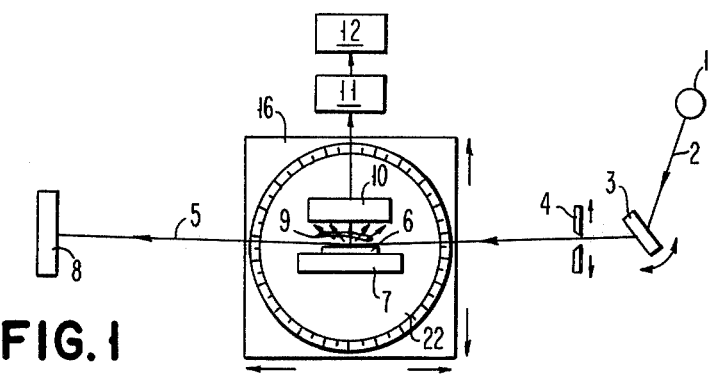
FIG. 1 is a basic schematic drawing in the manner of a block diagram of the x-ray fluorescence analysis apparatus as disclosed by the invention.

From the primary radiation 2 (e.g. Mo-K) emitted from an x-ray source 1 (FIG. 1), a parallel beam is formed in transmission radiation and having a residual divergency of approximately 3", for instance, by a displacement-free Si-monocrystal 3, which, as indicated by the arrow, is arranged rotatably round its center in the drawing plane. Via a diaphragm 4 which, as equally indicated by the arrows, can be slidably arranged, the beam is directed to a sample 6 at an angle of incidence which corresponds to the total reflection conditions of the incident primary beams 2. Since this sample 6 reflects in the form of scattering radiation 5, the majority of the incident primary beams 2 can be made incident on the absorbing medium 8 which can, for example, be a lead plate. The angle of incidence of the incident primary beams 2 can be set between several seconds and 1° to 2°, which is achieved by fixing sample 6 on goniometer 22.

In order to be able to set the point of incidence on the sample surface in the respective position required for sample support table 7, as indicated by the arrows, can be shifted to the left or the right. Similarly, but not shown, sample table 7 can also be shifted perpendicularly to the drawing plane. Primary beams 2, however, are not reflected at the sample surface itself but, depending on the angle of incidence, penetrate more or less deeply into sample 6. The penetration depth is determined by the deviation of the angle of incidence from the angle of the total reflection with predetermined sample material. The thus excited characteristic x-ray fluorescence radiation 9 is detected by a suitable wide angle beam detector 10 to be converted into an electric quantity which, amplified by an amplifier 11, is in turn applied to evaluator 12. Beam detector 10 should advisably and advantageously be designed as energy-dispersive wide angle detector which can cover a maximum solid angle, provided no light elements, as boron, are to be analyzed.

Practical use has shown that the analyzing depth can be typically varied by two powers of ten depending on the manner used by slightly altering the angle of incidence of primary radiation 2 accordingly.

Although for obtaining highly parallelized primary x-ray beams 2 directed on sample 6, the use of a tiltable crystal 3 is shown in the drawing which is passed through by primary x-ray beams 2, and the use of a crystal is suggested at which primary x-ray beams 2 are reflected under Bragg reflection conditions to be subsequently sharply focused through diaphragm 4 on to sample 6. Primary x-ray beams 2, instead of following this parallelization method, can also be directed via a collimator inserted between x-ray source 1 and sample 6, as specified below in detail in connection with the embodiment according to FIG. 3.

Wide angle beam detector 10 is shown in FIG. 1 as a lithium drifted silicon detector. Depending on the respective use, it is equally possible to employ other beam detectors which will then have to be adapted to the respective measuring process.

It is furthermore advisable for the examination of samples containing elements with low atomic numbers Z, to provide the x-ray source and sample together, in an evacuated or helium-filled chamber, in order to avoid, above all, an x-ray beam absorption between detector and sample.

For that purpose, however, the second goniometer 14 (FIG. 2) has, of course, to be arranged within chamber 30. For samples containing elements of a higher atomic number Z, no such chamber 30 is, of course, required. If an electron synchroton is used as a source of high x-ray beam intensity, an extremely high detection sensitivity is reached also when monocrystal 3 is used for parallelizing primary beam 2; on the other hand, however, this crystal 3 does not have to be used in that case.

As indicated in the publication "Service Studies of Solids by Total Reflection of X-Rays" by L. G. Parratt in the Journal "Physical Review", Vol. 95, No. 2, pages 359 to 369 (1954), FIG. 5 on page 361, the penetration depth of a primary x-ray of $\lambda = 1.39$ Å into a Cu sample at a glancing angle is approximately 150 Å. Thus, the characteristic x-ray fluorescence radiation is excited only within 150 Å under the surface, and it is then according to the invention detectable by beam detector 10 to be registered and identified via an amplifier 11 in evaluator 12. If, in this example, primary beam 2 is made to impinge at half a glancing angle, the information depth is 20 Å only; but with an angle of impingement of 1.5-fold, the amount of the glancing angle 2000 Å is obtained. It is thus shown that according to the respective use involved, the analyzing depth can be varied by two powers of ten in that the angle of impingement of primary x-ray radiation 2 is slightly altered accordingly.

However, this permits advantageous uses for a great variety of measurements. A doping profile in semiconductors can be determined in a destruction-free manner. Owing to the invention, this permits an intermediate measuring process in semiconductor component production, permitting a direct intervention in the production parameters, depending on the result of the intermediate measuring. If the invention is applied in such a manner, it is therefore no longer necessary either to interrupt the production of the semiconductor components, or to tolerate further production of defective semiconductor components prior to the respective revision of the process parameters, so that the production is considerably facilitated and accelerated.

As another possibility, the examination of those samples should be mentioned where a substrate with elements contained therein is covered by a layer which in turn carries a thin film consisting of elements contained in the substrate. Since, owing to the invention, the penetration depth into the sample to be examined can be restricted as required, a surface analysis undisturbed by background radiation is also possible which hitherto could not be carried out since the background radiation of the substrate would not have permitted a clear determination of the thin film composition on the surface. Such a possibility which is offered by the invention is of particular importance also in the production of semiconductor components if it is taken into consideration that silicon substrates or integrated semiconductor circuits in silicon generally have an aluminum metallization in their surface for providing the required supply lines to the semiconductor components contained therein. This aluminum metallization generally contains a silicon thin film coating. Hitherto, inspection and examination of such coatings was highly complicated and complex. By means of the process as disclosed by the invention, however, the characteristics of this thin film coating can be determined in a very simple manner. By means of the apparatus, as disclosed by the invention, it is finally possible to detect and identify also surface impurities on semiconductor components, which is of advantage in connection with field effect transistors, charge-coupled semiconductor components etc., and in their manufacture.

Figure 2:
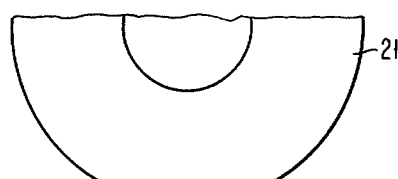
FIG. 2 is a schematic drawing with open examination chamber, shown in a plan view of the arrangement as disclosed by the invention.

In the embodiment shown schematically in FIG. 2, the apparatus as disclosed by the invention is installed in an examination chamber 30 whose wall 15 shows an evacuation stub 31. Outside chamber 30, there is a second goniometer 14 with an x-ray tube 1 fixed to its edge in such a manner that a primary x-ray beam 2 can impinge under a predetermined angle on parallelization crystal 3. This parallelization crystal 3 is fixed by means of sample holder 13 on sample table 27 with its main surface disposed vertically to the goniometer plane. Furthermore, second goniometer 14 shows diaphragm 4 whose fixing strip shows a slot through which, by means of a screw, it slidably fixed to the goniometer. If necessary, a diaphragm 4 can be employed whose slot width can be altered. At any rate, the position of diaphragm 4 can be fixed in such a manner that the respective parts of primary x-ray radiation 2 can be blocked out. Through a window 32 in examination chamber 30, x-ray beam 2 is incident on first goniometer 22 which is fixed on a table 16 displaceable as indicated by the arrows. First goniometer 22 carries a sample table 17 whose height can be altered by turning the center column provided, but not shown. Window 32 for the passage of x-ray radiation 2 can consist of a material suitable for that purpose, as for example beryllium.

Sample table 17 carries sample holder 7 holding sample 6 with its main surface perpendicularly to the plane of sample table 17. Since goniometer table 16 can be displaced, and sample table 17 can be adjusted in its height, the primary x-ray radiation can be incident on any required position of the sample 6 surface.

Also, the angle of incidence can be varied due to the goniometer turning. The directing of the beam onto the sample is reliably ensured in a suitable manner when the evacuated or helium-filled chamber 20 and second goniometer 14, with x-ray source 1 fixed thereon and parallelization crystal 3 provided thereon, and with diaphragm 4 are fixed in a manner known per se on a joint support not shown.

Characteristic x-ray fluorescence radiation 9 reflected by sample 6 is detected by a beam detector provided in holding device 19, preferably a lithium-drifted silicon crystal, and transduced into an electric quantity. Beam detector holding device 19 is fixed to a cooling finger 18 protruding through examination chamber wall 15, that cooling finger 18 itself protruding into a Dewar vessel to be cooled down to the temperature of a liquid nitrogen.

Outside examination chamber 30, cooling finger 18 supports preamplifier 20 fixed to cooling finger or column 18 by means of fixing elements 23. Via electric lines passing through cooling finger 18, this preamplifier 20 is connected with its input to the output of the beam detector. The output of preamplifier 20 is connected to an evaluator device not shown. The apparatus shown is preferably used for examining samples containing elements of higher atomic number, i.e. $Z > 11$, x-ray tube 1 emitting for example, an $Mo-K_\alpha$-lines.

The electric lines required for operating x-ray tube 1 pass through the base of the center column of goniometer 14, through the goniometer disc to the fixing element of x-ray tube 1, and through the latter. Since the goniometer column is hermetically connected to the floor of the examination chamber, a perfect operation of the arrangement, as disclosed by the invention, is ensured also when examination chamber 30 is evacuated, although second goniometer 14 is housed in chamber 30.

Figure 3:
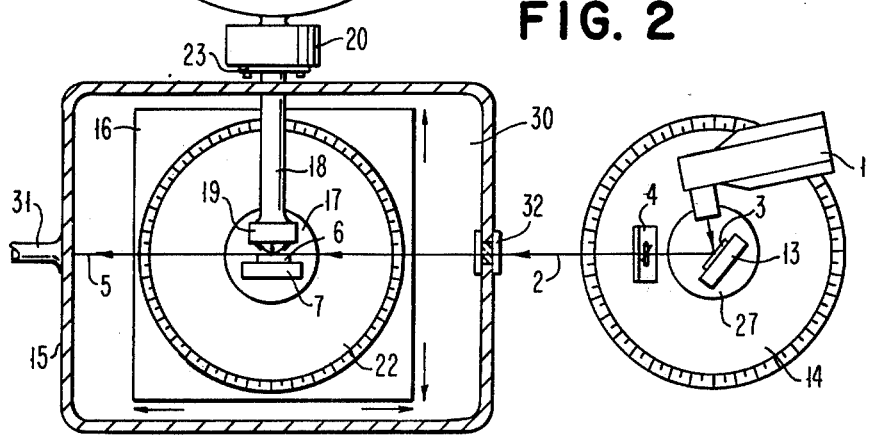
FIG. 3 shows another embodiment of the invention in schematic plan view with open examination chamber.
Figure 3:
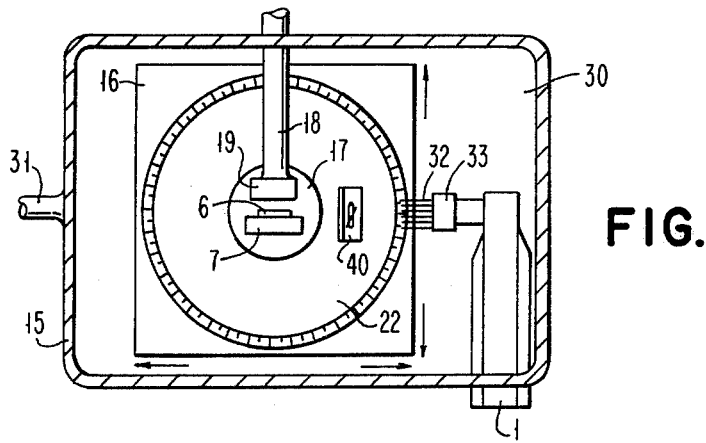

A less complicated way of realizing the arrangement as disclosed by the invention is shown in FIG. 3 since there, a collimator 32 is used instead of, as in the embodiment of FIG. 2, parallelization crystal 3 with x-ray diaphragm 4 arranged in series thereto. In this embodiment, x-ray tube 1 is inset into chamber wall 15 of examination chamber 30, and hermetically fixed there. This furthermore offers advantageous means of providing the electric operating lines, as due to the accessibility of x-ray tube 1 from the outside, no specific steps are required from outside examination chamber 30 for sealing said examination chamber 30.

By means of a fixing element 33, collimator 32 is applied at the output stub of x-ray tube 1. Collimator 32 itself can consist of several thin plates arranged in parallel and spaced at approximately 0.1 mm which are arranged in longitudinal direction to the primary x-ray beam. Here, too, a goniometer 22 is fixed on goniometer table 16 which is arranged in such a manner that it can be shifted in all directions. On goniometer 22, a height-adjustable sample table 17 is provided which carries sample holder 7 for keeping samples 6 with their main surface perpendicularly to the sample table plane. The table shift is indicated by respective arrows. Also, in this case, a beam detector mounted in beam detector holder 19 is used for detecting the characteristic x-ray fluorescence radiation. Beam detector holding device 19 is applied at cooling finger 18 which, through chamber wall 15, protrudes towards a Dewar vessel not shown. Via electric lines passing through cooling finger 18, beam detector 19 is connected to a preamplifier and evaluator not shown. By turning the sample by means of goniometer 22, as in the embodiment of FIG. 2, the angle of incidence of the primary x-ray radiation can be set to the sample surface. Since sample table 17 can be adjusted in height and goniometer table 16 can be shifted, each point of the sample surface can be scanned by the primary x-ray beam. As shown in the embodiment, the distance between collimator 32 and sample 6 can be reduced down to the possibilities given by the respective components. Here, too, examination chamber 30 is evacuated via stub 31 provided at chamber wall 15.

By means of the spectrograms shown in FIGS. 4 to 7, the results of a sample examination practically realized by means of the invention will be discussed. The sample used is a gallium phosphide substrate which is coated with an aluminum layer of a thickness of 8000 Å which in turn carries a silicon layer of a thickness of 100 Å. The x-ray source used is a molybdenum tube with an operating voltage of 40 keV and an operating current of 20 mA. Due to corresponding diaphragms, the parallelism of the primary x-ray beams is not lower than approximately 6'. The characteristic x-ray fluorescence radiation is detected with an Si-(Li) detector with an energy resolution of 170 eV below the above-mentioned cooling conditions; the measuring being, however, performed not under vacuum conditions but at atmospheric pressure in air. The distance between sample and detector is 25 mm.

Figure 4:
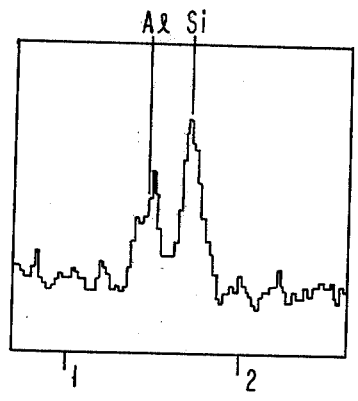
FIGS. 4 to 7 are spectrograms obtained at different angles of incidence of a sample of gallium phosphide with aluminum and silicon evaporated thereon.

The spectrogram according to FIG. 4 is made at an angle of incidence of 0.02°. This shows that a surface analysis by means of the invention can easily be limited to the upper 100 Å of the sample, as the vapor-deposited silicon coating in a thickness of 100 Å is preponderant as compared with the other spectral lines.

Figure 5:
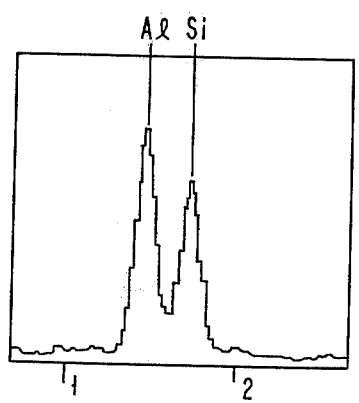

The spectrogram of FIG. 5 is made at an angle of incidence of 0.10°. It shows Al and Si spectral lines of almost the same shape, although aluminum layer thickness and silicon layer thickness are in a ratio of 80:1. This shows quite clearly that by means of the apparatus as disclosed by the invention, thin surface films can be analyzed independently of the substrate. The gallium and phosphorous lines of the substrate elements do not appear at all.

Figure 6:
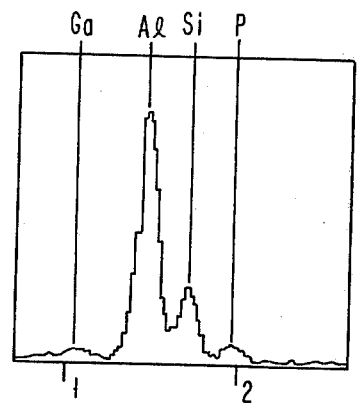

FIG. 6 shows the spectrum of the characteristic x-ray fluorescence radiation near the angle of incidence under total reflection conditions. The spectral lines of gallium and phosphorous, as elements of the substrate, are already faintly visible, but the spectral lines of aluminum and silicon still stand out clearly against them.

Figure 7:
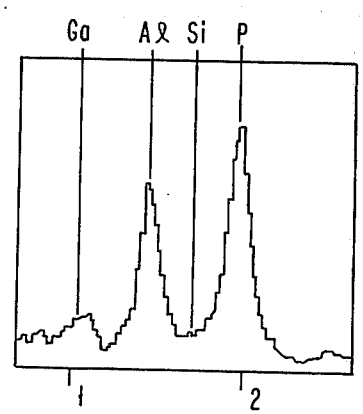

The spectrogram of FIG. 7 finally shows the result of a conventional x-ray fluorescence analysis. The most clearly defined lines are the P-spectral lines of the gallium phosphide substrate, as well as the Al-spectral lines. While the gallium lines are still clearly visible too, the silicon spectral lines have completely disappeared. They are fully covered in the trailing part of the spectral phosphorous lines.

The advantages of the process as disclosed by the invention, or of the apparatus as disclosed by the invention, respectively, can therefore be easily derived from the specified x-ray spectrograms obtained according to FIGS. 4 to 7. It it is taken into consideration that the parallelism of the primary x-rays as used for the above specified sample examination does, with approximately 6', not exactly show a particularly good quality but that the penetration depth could already be restricted to approximately 100 Å in the surface zone of the sample, it is quite evident that with an even higher parallelism of the primary x-rays incident on the sample, due for example to the use of a parallelism crystal, still better results can be obtained. If for instance, the parallelism of the primary x-rays would be brought to a value of 0.01', it is easily estimated that the analyzing depth in the surface zone can be reduced to 10 to 20 Å so that by means of the apparatus as disclosed by the invention, hitherto unobtainable resuls can be achieved.

While the invention has been particularly shown and described with reference to the preferred embodiments thereof, it will be understood by those skilled in the art that various changes in form and details may be made therein without departing from the spirit and scope of the invention.

What is claimed is:

1. An x-ray fluorescence analysis apparatus where highly parallelized x-rays are directable as primary beams under a predetermined angle onto a sample for exciting characteristic x-ray fluorescence beams which in turn are detectable by a beam detector for finding data on composition of elements of the respective excited layer thicknesses of the sample, comprising:

means for directing a primary x-ray beam to penetrate a surface adjacent portion of said sample at an angle of incidence not exceeding 2°, the scattering radiation reflected from said sample, at an angle corresponding to said angle of incidence being suppressed; and x-ray spectrometer means for limiting detection to substantially only x-ray fluorescences, of said sample, excited by said beam.

2. Apparatus as claimed in claim 1 wherein said sample comprises a semiconductor wafers.

3. Apparatus as claimed in claim 1 characterized in that synchrotron radiation comprises a source of said primary x-ray beam.

4. Apparatus as claimed in claim 1 wherein said spectrometer comprises a crystal spectrometer for analyzing the X-ray fluorescence radiation of light elements.

5. Apparatus as claimed in claim 1 wherein said spectrometer includes a lithium-drifted silicon crystal for said beam detection.

6. Apparatus as claimed in claim 5 characterized in that synchrotron radiation comprises a source of said primary x-ray beam.

7. Apparatus as claimed in claim 1 wherein said sample is disposed in a vacuum chamber and said spectrometer means includes an energy dispersive wide angle radiation detector mounted at an end of an optical column in said chamber with said column extending through a wall of said chamber and externally thereof into a Dewar vessel filled with liquified gas.

8. Apparatus as claimed in claim 7 characterized in that synchrotron radiation comprises a source of primary x-ray beam.

9. Apparatus as claimed in claim 7 including a collimator for parallelizing said primary x-ray beam.

10. Apparatus as claimed in claim 9 wherein said spectrometer includes a lithium-drifted silicon crystal as a beam detector.

11. Apparatus as claimed in claim 10 characterized in that a synchrotron radiation comprises a source of said primary x-ray beam.

* * * * *